USOO5414159A

United States Patent [19]
Appleton et al.

[11] Patent Number: 5,414,159
[45] Date of Patent: May 9, 1995

[54] PROCESS

[75] Inventors: Paul Appleton, Darlington; Michael A. Wood, Middlesbrough, both of England

[73] Assignee: Eastman Chemical Company, Kingsport, Tenn.

[21] Appl. No.: 174,320

[22] Filed: Dec. 30, 1993

[30] Foreign Application Priority Data

Dec. 2, 1993 [GB] United Kingdom ............... 9324785

[51] Int. Cl.$^6$ ..................... C07C 29/136; C07C 31/20
[52] U.S. Cl. ..................... 568/864; 568/831; 568/852
[58] Field of Search ............... 568/822, 823, 831, 864

[56] References Cited

U.S. PATENT DOCUMENTS 2,040,944 5/1936 Lazier .................... 568/864

(List continued on next page.)

FOREIGN PATENT DOCUMENTS

| 143634 | 6/1985 | European Pat. Off. . |
|---|---|---|
| 2417760 | 10/1987 | European Pat. Off. . |
| 301853 | 2/1989 | European Pat. Off. . |
| 353990 | 2/1990 | European Pat. Off. . |
| 378756 | 7/1990 | European Pat. Off. . |
| 552463 | 7/1993 | European Pat. Off. . |
| 1276722 | 10/1961 | France . |
| 1144703 | 3/1963 | Germany . |
| 1159925 | 12/1963 | Germany . |
| 2719867 | 11/1978 | Germany . |
| 3843956 | 6/1990 | Germany . |
| 4141199 | 6/1993 | Germany . |
| 988316 | 4/1965 | United Kingdom . |
| 1024318 | 3/1966 | United Kingdom . |
| 1454440 | 11/1976 | United Kingdom . |
| 1464263 | 2/1977 | United Kingdom . |
| 2116552 | 9/1985 | United Kingdom . |
| 2250287 | 6/1992 | United Kingdom . |
| 8203854 | 11/1982 | WIPO . |
| 8603189 | 6/1986 | WIPO . |
| 8607358 | 12/1986 | WIPO . |
| 8800937 | 2/1988 | WIPO . |
| 8900886 | 2/1989 | WIPO . |
| 9008121 | 7/1990 | WIPO . |
| 9101961 | 2/1991 | WIPO . |

OTHER PUBLICATIONS

Homer Adkins, "Catal. Hydrog. of Esters to Alcoh.", *Organic Reactions*, vol. 8, Chp. 1, pp. 2–27 (1954).

(List continued on next page.)

*Primary Examiner*—Werren B. Lone
*Attorney, Agent, or Firm*—J. Frederick Thomsen; Harry J. Gwinnell

[57] ABSTRACT

A process is described for the production of cyclohexanedimethanol by hydrogenation of a dialkyl cyclohexanedicarboxylate which comprises the steps of:

(a) providing a hydrogenation zone containing a charge of a granular reduced manganese promoted copper catalyst;
(b) forming a vaporous feed stream of a hydrogenatable material comprising a dialkyl cyclohexanedicarboxylate and from about 0.1 wt % up to about 15 wt % of an acidic material at a feed temperature which is in the range of from about 150° C. to about 350° C. and which is above the dew point of the feed stream and at a feed pressure which is in the range of from about 150 psia (about 10.34 bar) up to about 2000 psia (about 137.90 bar), said vaporous mixture having a known hydrogen-containing gas:dialkyl cyclohexanedicarboxylate ratio;
(c) supplying the vaporous feed stream to the hydrogenation zone;
(d) maintaining hydrogenation conditions in the hydrogenation zone which are effective to maintain the reaction mixture in contact with the catalyst above its dew point;
(e) passing the vaporous feed stream through the hydrogenation zone: and
(f) recovering from the hydrogenation zone a product stream comprising cyclohexanedimethanol.

17 Claims, 2 Drawing Sheets

U.S. PATENT DOCUMENTS

| | | | |
|---|---|---|---|
| 2,079,414 | 5/1937 | Lazier | 568/864 |
| 2,091,800 | 8/1937 | Adkins et al. | 568/864 |
| 2,105,664 | 1/1938 | Lazier | 568/864 |
| 2,137,407 | 11/1938 | Lazier | 568/864 |
| 2,755,317 | 7/1956 | Kassel | 568/814 |
| 2,818,393 | 12/1957 | Lefrancois et al. | 252/466 |
| 2,830,095 | 4/1958 | Nicolaisen | 568/841 |
| 2,884,450 | 4/1959 | Holmquist | 568/864 |
| 2,901,466 | 8/1959 | Kibler et al. | 568/864 |
| 2,917,549 | 12/1959 | Hasek et al. | 568/831 |
| 3,334,149 | 8/1967 | Akin et al. | 568/864 |
| 4,032,458 | 6/1977 | Cooley et al. | 568/864 |
| 4,052,467 | 10/1977 | Mills et al. | 568/864 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/864 |
| 4,751,334 | 6/1988 | Turner et al. | 568/864 |
| 4,837,368 | 6/1989 | Gustafson et al. | 568/881 |
| 4,847,425 | 7/1989 | Degner et al. | 568/831 |
| 4,880,937 | 11/1989 | Matsushita et al. | 568/831 |
| 4,929,777 | 5/1990 | Irick, Jr. et al. | 568/864 |
| 4,999,090 | 3/1991 | Tateno et al. | 203/36 |
| 5,030,771 | 7/1991 | Fuhrmann et al. | 568/814 |
| 5,124,435 | 6/1992 | Mori et al. | 528/307 |
| 5,142,067 | 8/1992 | Wegman et al. | 549/336 |
| 5,185,476 | 2/1993 | Gustafson | 568/831 |
| 5,191,091 | 3/1993 | Wegman et al. | 549/326 |

OTHER PUBLICATIONS

Mansour et al., "Sel. Hydrog. of Esters to Alcoh. with a Catal. Obtained $Rh_2O_3$, $Sn(n-C_4H_9)_4$ and $SiO_2$ and Based on Isol. Active Centres", *Angew. Chem.* 101, (1989), No. 3, 360–63.

Wehner & Gustafson, "Catalystic Hydrog. of Esters Over Pd/ZnO", *Journ. of Catalysis*, 135, 420–426 (1992).

Lewin et al., "Fiber Chemistry", pp. 8–9 (1985).

PROCESS

FIELD OF THE INVENTION

This invention relates to a process for the production of cyclohexanedimethanol.

BACKGROUND OF THE INVENTION 1,4-cyclohexanedimethanol is used to prepare highly polymeric linear condensation polymers by reaction with terephthalic acid and is useful as an intermediate in the preparation of certain polyester and polyester amides. The use of 1,4-cyclohexanedimethanol for such purposes is disclosed in, for example, U.S. Pat. No. 2,901,466. This document teaches that the trans-isomer of polycyclohexylenedimethylene terephthalate has a higher melting point range (315°–320° C.) than the corresponding cis-isomer (260°–267° C.).

One method for preparing 1,4-cyclohexanedimethanol (hexahydroterephthalyl alcohol) involves the hydrogenation of diethyl 1,4-cyclohexanedicarboxylate (diethyl hexahydroterephthalate) in a slurry phase reactor in the presence of a copper chromite catalyst at a pressure of 3000 psia (about 206.84 bar) and a temperature of 255° C., as is described in Example 3 of U.S. Pat. No. 2,105,664. The yield is said to be 77.5%.

The hydrogenation of dimethyl 1,4-cyclohexanedicarboxylate (DMCD) to 1,4-cyclohexanedimethanol (CHDM) is shown below in equation (1):

melting point for such materials is considered desirable. As noted above, the trans-isomer of a typical polyester, such as trans-polycyclohexylmethyl terephthalate, has a higher melting point than the cis-isomer. Hence, for example, U.S. Pat. No. 5,124,435 discloses a polyester copolymer, the 1,4-cyclohexanedimethanol content of which has a trans-isomer content of at least 80 mole %, and which has a high heat resistance. The preferment of trans-1,4-cyclohexanedimethanol over cis-1,4-cyclohexanedimethanol is also discussed in U.S. Pat. No. 2,917,549, in U.S. Pat. No. 4,999,090 and in GB-A-988316.

A liquid phase process for the production of 1,4-cyclohexanedimethanol by plural stage hydrogenation of dimethyl terephthalate is described in U.S. Pat. No. 3,334,149. This utilises a palladium catalyst to effect hydrogenation of dimethyl terephthalate to dimethyl 1,4-cyclohexanedicarboxylate, followed by use of a copper chromite catalyst in the liquid phase to catalyse the hydrogenation of that diester to 1,4-cyclohexanedimethanol. In the procedure described in Example 1 of that patent specification a residence time of about 40 to 50 minutes is used in the second stage of this process. The activity of the copper chromite catalysts recommended in U.S. Pat. No. 3,334,149 is such that long residence times are required. It is stated at column 16 line 72 et seq.: "We have found that the copper chromite hydrogenation catalyst is sensitive to the presence of the monoalkyl ester of 1,4-cyclohexanedicarboxylic

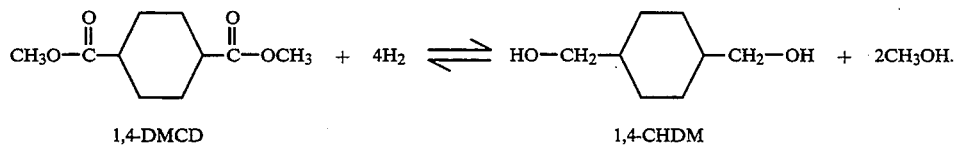

1,4-DMCD          1,4-CHDM

The two geometrical isomers of CHDM thus produced are:

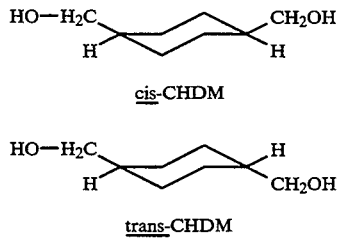

cis-CHDM trans-CHDM

The resulting 1,4-cyclohexanedimethanol product is a mixture of these two isomers which have different melting points. As reported on page 9 of the book "Fiber Chemistry" edited by Menachem Lewis and Eli M. Pearce, published by Marcel Dekker, Inc.: "Both the alicyclic ester [i.e. dimethyl 1,4-cyclohexanedicarboxylate] and the alicyclic diol [i.e.1,4-cyclohexanedimethanol] exist in two isomeric forms, cis . . . and trans . . . , that are not interconvertible without bond rupture". The passage continues later: "Control of the [cis-:trans-] ratio is important [in 1,4-cyclohexanedimethanol] since many polymer and fiber properties depend on it".

The cis-isomer of 1,4-cyclohexanedimethanol has a melting point of 43° C. and the trans has a melting point of 67° C. The higher melting point trans-isomer is often preferred over the cis-isomer for use as a reagent in the preparation of polyester and polyester-amides if a high acid (referred to for brevity as the "acid-ester") which is formed as a by-product in the first hydrogenation stage. Our investigations have shown that concentrations of the acid-ester up to about 2 weight percent in the feed for the copper chromite can be tolerated. However, with substantially larger concentrations, e.g., 5 weight percent, of acid-ester in the dialkyl cyclohexanedicarboxylate feed the activity of the copper chromite catalyst decreases markedly".

In a liquid phase process for the production of 1,4-cyclohexanedimethanol, such as is disclosed in U.S. Pat. No. 3,334,149, the trans-:cis- isomer ratio of the product 1,4-cyclohexanedimethanol will tend towards an equilibrium value. This equilibrium value has been reported variously and may lie between about 2.57:1 (trans-:cis- 1,4-cyclohexanedimethanol) (as reported in GB-A-988316) and about 3:1 (as reported in U.S. Pat. No. 2,917,549). However, the starting material, dimethyl 1,4-cyclohexanedicarboxylate, is generally commercially obtainable as a mixture of cis- and trans-isomers wherein there is a preponderance of the cis-isomer. Thus in a typical commercial grade of dimethyl 1,4-cyclohexanedicarboxylate the trans-:cis- isomer ratio is from about 0.5:1 to about 0.6:1.

Attempts to deal with the problem of the presence of an excess of the less desirable cis-1,4-cyclohexanedimethanol isomer in any process for 1,4-cyclohexanedimethanol manufacture have focused on the isomerisation of the cis-isomer of cyclohexanedimethanol to the trans-isomer thereof.

U.S. Pat. No. 2,917,549 discloses a process for isomerising cis-1,4-cyclohexanedimethanol to trans-1,4-cyclohexanedimethanol which comprises heating cis-1,4-cyclohexanedimethanol at a temperature of at least 200° C. in the presence of an alkoxide of a lower atomic weight metal such as lithium, sodium, potassium, calcium or aluminium. However, the process of U.S. Pat. No. 2,917,549 necessarily involves a two-stage process wherein the initial cis-/trans- 1,4-cyclohexanedimethanol hydrogenation product is recovered from the hydrogenation zone and subjected to temperatures in excess of 200° C. in the presence of a metal alkoxide catalyst under an atmosphere of nitrogen. The capital and operational costs associated with a plant designed to carry out the process taught in U.S. Pat. No. 2,917,549 would be undesirably high. Another disadvantage of such a plant is the associated hazard relating to the use of metal alkoxides as catalysts in the isomerisation zone. Such catalysts are required to effect the isomerisation, which is reported not to occur under typical hydrogenation conditions using hydrogenation catalysts such as copper/chrome or Raney nickel catalysts, according to the teaching of Example 11 of U.S. Pat. No. 2,917,549. Furthermore, steps would be required to prevent product contamination by the metal alkoxide catalyst.

U.S. Pat. No. 4,999,090 discloses a process for the isomerisation of cis-1,4-cyclohexanedimethanol by distillation in the presence of an alkali metal hydroxide or alkoxide at a temperature of between 150° C. and 200° C. and at a pressure of between 1 mm Hg and 50 mm Hg (between 1.33 millibar and 66.5 millibar). This process has very similar disadvantages to those of U.S. Pat. No. 2,917,549.

GB-A-988316 teaches a process for the preparation of trans-1,4-cyclohexanedimethanol in which a mixture of cis- and trans-isomers of dimethyl hexahydroterephthalate (i.e. dimethyl 1,4-cyclohexanedicarboxylate) is hydrogenated at elevated temperature and pressure in the presence of a Cu/Zn catalyst. Trans-1,4-dimethylolcyclohexane (i.e. trans-1,4-cyclohexanedimethanol) is separated by crystallisation from the reaction product and then the residual product, now enriched in cis-1,4-cyclohexanedimethanol, is recycled to the hydrogenation zone whereupon it undergoes isomerisation to a cis-/trans- 1,4-cyclohexanedimethanol mixture. The recycle procedure may be repeated to obtain a 1,4-cyclohexanedimethanol product containing the trans-isomer in substantial excess. However, the process according to GB-A-988316 is more preferably operated under conditions such that recycled cis-isomer enriched product is combined with fresh dimethyl 1,4-cyclohexanedicarboxylate feed on re-entry to the hydrogenation zone. The effectiveness of recycling the cis-isomer to the hydrogenation zone is largely a result of the dual function of the copper/zinc catalyst which possesses both a hydrogenating and an isomerising catalytic action. As would be expected from thermodynamic principles, the isomerising action is most effective when a mixture containing a preponderance of the cis-isomer is recycled to the hydrogenation zone. However, recycling the cis-isomer in this way is acknowledged to cause a new problem, that of the formation of unwanted by-products, such as 1-methyl-4-hydroxymethylcyclohexane, which may be formed by operating the hydrogenation reaction under too severe conditions. To minimise the formation of such by-products, the hydrogenation zone may be operated under "relatively mild conditions", according to the teaching of GB-A-988316 (see, for example page 2, lines 55 to 79 of GB-A-988316). However, such mild conditions reduce the achieved conversion of dimethyl 1,4-cyclohexanedicarboxylate with the result that, for any one pass through the hydrogenation zone, a significant quantity of dimethyl hexahydroterephthalate (dimethyl 1,4-cyclohexanedicarboxylate) remains unconverted. By the term "relatively mild conditions" is meant a temperature of at least 200° C., preferably between 240° C. and 300° C., and a pressure of 200 to 300 atmospheres (202.65 bar to 303.98 bar), according to page 2, lines 26 to 32 of GB-A988316. The use of such high pressures at these elevated temperatures can be hazardous, besides requiring reactors with thick walls and flanges of special alloy constructed to withstand such extreme pressures. Hence it is expensive to construct a plant to operate at pressures as high as envisaged in GB-A-988316. Furthermore it is potentially hazardous to operate a plant operating at 200 atmospheres (202.65 bar) or above, as well as being very expensive, not only in terms of the capital cost of the plant but also with regard to operating costs. A substantial proportion of this capital cost is associated with the rigorous safety precautions that must be taken when operating a high pressure conventional commercial scale hydrogenation plant. It is also expensive to compress gaseous streams to such high pressures and to circulate them through the plant.

Although there is a passing reference (see page 1, line 84 of GB-A-988316) to use of "the gaseous phase", even at temperatures of 300° C. both cis- and trans- dimethyl hexahydroterephthalate would be in the liquid phase at pressures of 200 to 300 atmospheres (202.65 bar to 303.98 bar) at the hydrogen:ester ratio envisaged in the Examples. Thus in each of the Examples of GB-A-988316 liquid phase conditions are used. According to Example 4, which uses a feed mixture containing dimethyl hexahydroterephthalate (i.e. 1,4-dimethyl cyclohexanedicarboxylate), and methanol such as might be used in a recycling process, the isomers present in the diol in the hydrogenation product are stated to represent an equilibrium mixture of about 72% of the trans- and about 28% of the cis-isomer, i.e. a trans-:cis-ratio of about 2.57:1.

It is known to effect hydrogenation of certain esters and diesters in the vapour phase. For example it has been proposed to use a reduced copper oxide/zinc oxide catalyst for effecting hydrogenation of esters in the vapour phase. In this connection attention is directed to GB-B-2116552. Also of relevance is WO-A-90/8121.

It is further known to produce diols, such as butane-1,4-diol, by catalytic hydrogenation of esters of dicarboxylic acids, such as a dimethyl or diethyl ester of maleic acid, fumaric acid, succinic acid, or a mixture of two or more thereof. Such processes are described, for example, in GB-A-1454440, GB-A-1464263, DE-A-2719867, U.S. Pat. No. 4,032,458, and U.S. Pat. No. 4172961.

Production of butane-1,4-diol by vapour phase hydrogenation of a diester, typically a dialkyl ester, of a $C_4$ dicarboxylic acid selected from maleic acid, fumaric acid, succinic acid, and a mixture of two or more thereof has been proposed. In such a process the diester is conveniently a di-($C_1$ to $C_4$ alkyl) ester, such as dimethyl or diethyl maleate, fumarate, or succinate. A further description of such a process can be found in U.S. Pat. No. 4,584,419, EP-A-0143634, WO-A-86/03189, WO-A-86/07358, and WO-A-88/00937.

In all of the above-mentioned vapour phase processes the esters or diesters all have a vapour pressure which is high compared to the vapour pressure of dimethyl 1,4-cyclohexanedicarboxylate and 1,4-cyclohexanedimethanol.

Because of the sensitivity of the conventionally used copper chromite catalysts to the presence of acidic impurities in the dimethyl 1,4-cyclohexanedicarboxylate feed material in a conventional liquid phase hydrogenation process it is usual to purify the feed material to remove at least most of the acidic impurities present in the dimethyl 1,4-cyclohexanedicarboxylate feedstock.

It would be advantageous to be able to use for the production of cyclohexanedimethanol a relatively impure dimethyl cyclohexanedicarboxylate feedstock which still has a significant content of the acidic impurity methyl hydrogen cyclohexanedicarboxylate.

SUMMARY OF THE INVENTION

It is accordingly an object of the present invention to provide a process for the production of cyclohexanedimethanol by hydrogenation of a dialkyl cyclohexanedicarboxylate, for example dimethyl cyclohexanedicarboxylate, having a significant content of the corresponding alkyl, e.g. methyl, hydrogen cyclohexanedicarboxylate and/or cyclohexanedicarboxylic acid. It further seeks to provide such a process which can be operated with substantially increased safety and operating economy at relatively low pressures. Another object of the invention is to provide a process for production of cyclohexanedimethanol by hydrogenation of an acidic grade of dialkyl cyclohexanedicarboxylate wherein the hydrogenation step yields directly from a cis-rich dialkyl cyclohexanedicarboxylate a cyclohexanedimethanol product with a higher trans-:cis- isomer ratio than is achievable by conventional hydrogenation methods. Hence it is a still further object of the invention to avoid the increased capital and operating costs of the prior art processes mentioned above which require the use of extreme hydrogenation conditions or a separate isomerisation step. It is also an object of the present invention to provide a process wherein a mixture of cis- and trans- isomers of dimethyl 1,4-cyclohexanedicarboxylate with a significant acid content is reacted rapidly and without appreciable loss of catalyst activity with high conversion and high selectivity to a mixture of cis- and trans-isomers of 1,4-cyclohexanedimethanol.

According to the present invention there is provided a process for the production of cyclohexanedimethanol by hydrogenation of a dialkyl cyclohexanedicarboxylate which comprises the steps of:

(a) providing a hydrogenation zone containing a charge of a granular reduced manganese promoted copper catalyst;

(b) forming a vaporous feed stream of a hydrogenatable material comprising a dialkyl cyclohexanedicarboxylate and from about 0.1 wt % up to about 15 wt % of an acidic material at a feed temperature which is in the range of from about 150° C. to about 350° C. and which is above the dew point of the feed stream and at a feed pressure which is in the range of from about 150 psia (about 10.34 bar) up to about 2000 psia (about 137.90 bar), said vaporous mixture having a known hydrogen-containing gas:dialkyl cyclohexanedicarboxylate ratio;

(c) supplying the vaporous feed stream to the hydrogenation zone;

(d) maintaining hydrogenation conditions in the hydrogenation zone which are effective to maintain the reaction mixture in contact with the catalyst above its dew point;

(e) passing the vaporous feed stream through the hydrogenation zone: and (f) recovering from the hydrogenation zone a product stream comprising cyclohexanedimethanol.

The invention is based upon the surprising discovery that, not only is the conversion of the starting material, i.e. dialkyl cyclohexanedicarboxylate, to the product, i.e. cyclohexanedimethanol, extremely rapid under the vapour phase hydrogenation conditions used, requiring only a matter of a few seconds for substantially complete conversion to occur, but also the isomerisation of 1,4-cyclohexanedimethanol that occurs in passage through the hydrogenation zone is comparably rapid. This is a surprising finding since two separate reactions are involved. Thus, for example, when the hydrogenatable material comprises a cis-rich dimethyl 1,4-cyclohexanedicarboxylate having a trans-:cis- isomer ratio of less than about 1:1, e.g. about 0.5:1 to about 0.6:1, a high trans-:cis- 1,4-cyclohexanedimethanol ratio, typically greater than about 2.0:1 up to about 3.84:1, as well as essentially complete conversion of dialkyl 1,4-cyclohexanedicarboxylate to 1,4-cyclohexanedimethanol, can be achieved by using a residence time of less than about a minute of the reaction mixture in the hydrogenation zone, typically in the range of from about 2 to about 15 seconds. This residence time is in stark contrast to the extended residence times recommended in the prior art, such as the 40 to 50 minutes residence time used in Example 1 of U.S. Pat. No. 3,334,149.

By the term "residence time" we mean the time taken for the reaction mixture at the temperature and pressure conditions used in the hydrogenation zone to pass through the empty volume of reactor occupied by the catalyst.

It is also surprising to find that, although the prior art teaches that acidic materials, such as alkyl (e.g. methyl) hydrogen cyclohexanedicarboxylate, have a deleterious effect upon copper-containing catalysts, such as copper chromite, in liquid phase operation, yet the presence of very significant amounts of such acidic materials, i.e. from about 0.1 wt % up to about 15 wt %, can be tolerated in the feed dialkyl (e.g. dimethyl) cyclohexanedicarboxylate when using a reduced manganese promoted copper catalyst under the vapour phase hydrogenation conditions of the process of the present invention, without significant loss of catalyst activity.

The process of the invention is operated using vaporous feed conditions with the feed stream being supplied to the hydrogenation zone in essentially liquid free vaporous form. Hence the feed stream is supplied to the hydrogenation zone at a feed temperature which is above its dew point. The process is further operated so that vapour phase conditions exist throughout the hydrogenation zone. Thus it is essential that the feed stream be at a temperature above its dew point at the inlet end of the catalyst bed if the advantage of vapour phase feed conditions is to be realised. The use of vapour phase feed conditions in the process of the invention has the advantage that, compared with liquid phase operation of the process, generally lower operating pressures can be used. This generally has a significant and beneficial effect not only on the construction costs but also on the operating costs of the plant.

In the hydrogenation zone the hydrogenatable material undergoes extremely rapid hydrogenation to yield cyclohexanedimethanol, as exemplified by equation (1) above. In addition, a comparably fast isomerisation reaction occurs under the hydrogenation conditions used. Hence a hydrogenatable material rich in cis-dimethyl cyclohexanedicarboxylate tends to yield a 1,4-cyclohexanedimethanol that has a higher content of the trans-isomer thereof than the trans-content of the starting diester.

In the case of hydrogenation of a cis-isomer rich dimethyl 1,4-cyclohexanedicarboxylate, i.e. a material with a trans-:cis isomer ratio of less than about 1:1, we have found that the trans-:cis- isomer ratio of the 1,4-cyclohexanedimethanol present in the reaction product mixture can be as high as approximately 3.84:1 under vapour phase hydrogenation conditions. This ratio is significantly higher than the ratio of between 2.57:1 and 3:1 which is reported to be achieved with such a cis-rich dimethyl 1,4-cyclohexanedicarboxylate feedstock under liquid phase reaction conditions at low conversions.

In a preferred process the dialkyl cyclohexanedicarboxylate is a di-($C_1$ to $C_4$ alkyl) cyclohexanedicarboxylate, e.g. a dimethyl, diethyl, di-n- or -iso-propyl, or di-n-, -iso- or -sec-butyl cyclohexanedicarboxylate, more preferably dimethyl cyclohexanedicarboxylate. In an especially preferred process the dialkyl cyclohexanedicarboxylate is dimethyl 1,4-cyclohexanedicarboxylate.

The hydrogenatable material may contain from about 0.1 wt % up to about 15 wt %, more usually greater than about 2 wt % up to about 10 wt %, e.g. from about 2.5 wt % up to about 5 wt %, of an acidic material such as an alkyl (e.g. methyl) hydrogen cyclohexanedicarboxylate and/or cyclohexanedicarboxylic acid.

When using dimethyl 1,4-cyclohexanedicarboxylate feed there may be used any feedstock containing a significant quantity of dimethyl 1,4-cyclohexanedicarboxylate. The feed ester dimethyl 1,4-cyclohexanedicarboxylate is commercially available as high purity dimethyl 1,4-cyclohexanedicarboxylate, technical grade dimethyl 1,4-cyclohexanedicarboxylate, cis-dimethyl 1,4-cyclohexanedicarboxylate, or trans-dimethyl 1,4-cyclohexanedicarboxylate. The preferred feedstock for the process of the invention is the technical grade dimethyl 1,4-cyclohexanedicarboxylate.

Whilst the process is used to advantage for the hydrogenation of dimethyl 1,4-cyclohexanedicarboxylate, it will be understood by those skilled in the art that the process of the invention may be equally well applied to the hydrogenation of any or all of the isomers of dimethyl cyclohexanedicarboxylate and mixtures thereof. Thus the process can be used with dimethyl 1,2-cyclohexanedicarboxylate containing, for example, methyl hydrogen 1,2-cyclohexanedicarboxylate and/or 1,2-cyclohexanedicarboxylic acid, dimethyl 1,3-cyclohexanedicarboxylate containing, for example, methyl hydrogen 1,3-cyclohexanedicarboxylate and/or 1,3-cyclohexanedicarboxylic acid, or dimethyl 1,4-cyclohexanedicarboxylate containing, for example, methyl hydrogen 1,4-cyclohexanedicarboxylate and/or 1,4-cyclohexanedicarboxylic acid.

In the prior art hydrogenation of dimethyl cyclohexanedicarboxylate has normally been carried out as a high pressure, liquid phase process. It is surprising that, despite the relatively high molecular weight and low vapour pressure of dimethyl cyclohexanedicarboxylate at temperatures below those at which some thermal decomposition is likely, e.g. below about 300° C., it is possible to design a viable commercial hydrogenation plant for hydrogenation of dimethyl cyclohexanedicarboxylate which utilises vapour phase feed conditions. It is moreover surprising that, although the prior art teaches that the presence of acidic materials in the dialkyl cyclohexanedicarboxylate feedstock deleteriously affects the activity of copper-containing catalysts, no such disadvantage appears to arise when using a reduced manganese promoted copper catalyst and vapour phase hydrogenation conditions.

It is surprising that the process of the invention can generate from a cis-rich dimethyl 1,4-cyclohexanedicarboxylate a 1,4-cyclohexanedimethanol product mixture whose trans-:cis-isomer ratio is in excess of the ratio that is the normal reported equilibrium ratio under liquid phase conditions. Thus, although the normal reported trans-:cis-isomer equilibrium ratio, under liquid phase conditions, can under favourable conditions be as high as about 3:1 when using a cis-rich dimethyl 1,4-cyclohexanedicarboxylate, the present invention, which operates with vaporous hydrogenation conditions, enables production in a single step from a cis-rich dimethyl 1,4-cyclohexanedicarboxylate of 1,4-cyclohexanedimethanol with a trans-:cis-isomer ratio as high as 3.84:1. When using trans-dimethyl 1,4-cyclohexanedicarboxylate the trans-:cis- isomer ratio of the 1,4-cyclohexanedimethanol product also tends towards the equilibrium ratio, i.e. about 3.84:1.

It is also surprising that the process of the invention can be operated for extended periods of up to several months or more, at high selectivity to the desired cyclohexanedimethanol product and at high conversion of the starting dialkyl cyclohexanedicarboxylate, since the prejudice in the art is that copper-containing ester hydrogenation catalysts would have only a short operating life and low activity at low operating pressures.

In the prior art it is made clear that the hydrogenation of dimethyl 1,4-cyclohexanedicarboxylate (dimethyl hexahydroterephthalate) is liable to give significant quantities of by-products. Thus GB-A-988316 acknowledges the problem caused by formation of unwanted by-products, such as 1-methyl-4-hydroxymethylcyclohexane. It is surprising to find that the process of the invention can be operated so that, despite the presence of a very large excess of hydrogen and the use of a very large vapour pressure of hydrogen compared to the relatively low vapour pressure of dimethyl cyclohexanedicarboxylate, the reaction proceeds rapidly with a very high conversion of dimethyl cyclohexanedicarboxylate to the desired product, i.e. cyclohexanedimethanol, but yet with a very high selectivity to that product and therefore with a very low yield of by-products. Thus under favourable conditions the conversion of dimethyl cyclohexanedicarboxylate to cyclohexanedimethanol can be as high as 98 mole % or higher with a selectivity to cyclohexanedimethanol of greater than 96 mole %. It is surprising to find that this occurs despite the presence of an impurity in the feedstock with a potentially damaging influence upon the activity of the catalyst.

In a commercial plant the process will normally be operated on a continuous basis. It may be preferred to employ at least two hydrogenation zones, each containing a charge of a heterogeneous ester hydrogenation catalyst, connected in parallel. Each of these zones is capable of independent isolation from the supply of vaporous feedstock mixture. Hence an isolated zone may be subjected to conditions substantially different from those prevailing in the remaining zone or zones, for example, whereunder the catalyst charge therein may be reactivated or replaced whilst the process of the invention is continued in the remaining zone or zones. This arrangement also permits operation under the conditions taught in WO-A-91/01961. In this case two hydrogenation reactors connected in parallel are used. In a first phase of operation with a fresh charge of catalyst one only of the reactors is used, the other one being in standby mode with the catalyst bathed in hydrogen. After a period of operation over which the catalyst activity may decline somewhat the second reactor is used, whilst the first one is placed in standby condition. After a further period of operation both reactors are used in parallel until the time comes to replace the entire catalyst charge.

The process of the invention is operated at a feed temperature of at least about 150° C. and no higher than about 350° C. The feed temperature is preferably in the range of from about 150° C. to about 300° C., most preferably from about 200° C. to about 260° C.

The feed pressure is in the range of from about 150 psia (about 10.34 bar) up to about 2000 psia (about 137.90 bar). However, the benefits and advantages of the present low pressure process utilising vaporous feed conditions are best realised by carrying out the process using a feed pressure of from about 450 psia (about 31.03 bar) up to about 1000 psia (about 68.95 bar).

The process requires that the vaporous feed stream is above its dew point so that the dialkyl (e.g. dimethyl) cyclohexanedicarboxylate is present in the vapour phase at the inlet end of the or each catalyst bed. This means that the composition of the vaporous feed stream must be controlled so that, under the selected operating conditions, the temperature of the feed stream at the inlet end of the or each catalyst bed is always above its dew point at the operating pressure. By the term "dew point" is meant that temperature at which a mixture of gases and vapours just deposits a fog or film of liquid. This dew point liquid will normally contain all the condensable components of the vapour phase, as well as dissolved gases, in concentrations that satisfy the usual vapour/liquid criteria. Typically the feed temperature of the vaporous feed stream to the hydrogenation zone is from about 5° C. up to about 10° C. or more above its dew point at the operating pressure.

A convenient method of forming a vaporous feed stream for use in the process of the invention is to spray liquid dialkyl (e.g. dimethyl) cyclohexanedicarboxylate or a dialkyl cyclohexanedicarboxylate solution into a stream of hot hydrogen-containing gas so as to form a saturated or partially saturated vaporous mixture. Alternatively such a vapour mixture can be obtained by bubbling a hot hydrogen-containing gas through a body of the liquid dialkyl cyclohexanedicarboxylate or dialkyl cyclohexanedicarboxylate solution. If a saturated vapour mixture is formed it should then be heated further or diluted with more hot gas so as to produce a partially saturated vaporous stream prior to contact with the catalyst.

In the process of the invention the hydrogen-containing gas:dialkyl (e.g. dimethyl) cyclohexanedicarboxylate molar ratio can vary within wide limits, depending upon the temperature and pressure. Although the major constituent of the hydrogen-containing gas is hydrogen, other gases may also be introduced, normally in minor amount, in the hydrogen-containing gas supplied to the process, such as nitrogen, argon, methane, and carbon oxides. In order to maintain the vaporous feed stream above its dew point at the inlet end of the or each catalyst bed at the operating pressure the hydrogen-containing gas:dialkyl (e.g. dimethyl) cyclohexanedicarboxylate molar ratio is desirably at least about 10:1 up to about 8000:1, preferably in the range of from about 200:1 to about 1000:1. Moreover the hydrogenation conditions are selected so as to maintain the reaction mixture in contact with the hydrogenation catalyst always above its dew point. Hence, when using dimethyl 1,4-cyclohexanedicarboxylate as the diester starting material, it is necessary to have regard to the fact that 1,4-cyclohexanedimethanol is less volatile than the diester starting material, dimethyl 1,4-cyclohexanedicarboxylate.

The hydrogen-containing gas used in the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the makeup gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, when using gas recycle, the gas recycle stream will normally contain minor amounts of an alkanol (e.g. methanol).

Although the process of the invention is operated with the feed stream in the vapour phase, it is convenient to express the feed rate of the hydrogenatable material to the hydrogenation zone as a space velocity and to express that space velocity as a liquid hourly space velocity. Hence it is convenient to express the feed rate in terms of the ratio of the liquid feed rate of the hydrogenatable material to the vaporisation zone to the volume of the hydrogenation catalyst. Thus the equivalent liquid hourly space velocity of the hydrogenatable material through the hydrogenation catalyst is preferably from about 0.05 to about 4.0 $h^{-1}$. In other words it is preferred to feed the liquid hydrogenatable material to the vaporisation zone at a rate which is equivalent to, per unit volume of catalyst, from about 0.05 to about 4.0 unit volumes of hydrogenatable material per hour (i.e. about 0.05 to about 4.0 $m^3h^{-1}$ per $m^3$ of catalyst). Even more preferably the liquid hourly space velocity is from about 0.1 $h^{-1}$ to about 1.0 $h^{-1}$. If the hydrogenatable material is a solid at ambient temperatures, then it may be necessary to heat it sufficiently to melt it or to dissolve it in a suitable inert solvent, in which latter case the solvent is ignored for the purpose of measuring the liquid hourly space velocity.

It will be readily apparent to those skilled in the art that the rate of passage of the vaporous feed stream through the hydrogenation zone will depend upon the feed rate of the hydrogenatable material to the vaporisation zone and upon the hydrogen-containing gas:hydrogenatable material molar ratio.

The granular catalyst used in the process of the invention may be formed into any suitable shape, pellets, rings or saddles.

The catalyst used in the process of the present invention is a reduced manganese promoted copper catalyst. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89 which is available from Davy Research and Development Limited, P.O. Box 37, Bowesfield Lane, Stockton-on-Tees, Cleveland TS18 3HA, England.

Any recognised supporting medium may be used to provide physical support for the catalyst used in the process of the invention. This support can be provided by materials such as zinc oxide, alumina, silica, aluminasilica, silicon carbide, zirconia, titania, carbon, a zeolite, or any suitable combination thereof.

The or each hydrogenation zone may comprise a shell-and-tube reactor which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such an adiabatic reactor may contain a single charge of a hydrogenation catalyst or may contain two or more beds of catalyst, or beds of different hydrogenation catalysts. If desired, external or internal inter-bed heat exchangers may be provided in order to adjust the inlet temperature to one or more beds of catalyst downstream from the inlet to the adiabatic hydrogenation reactor.

The invention is further described with reference to the following Examples. The compositions of catalysts A and B used in the Examples are listed in Table I.

EXAMPLE 1

Figure 1:
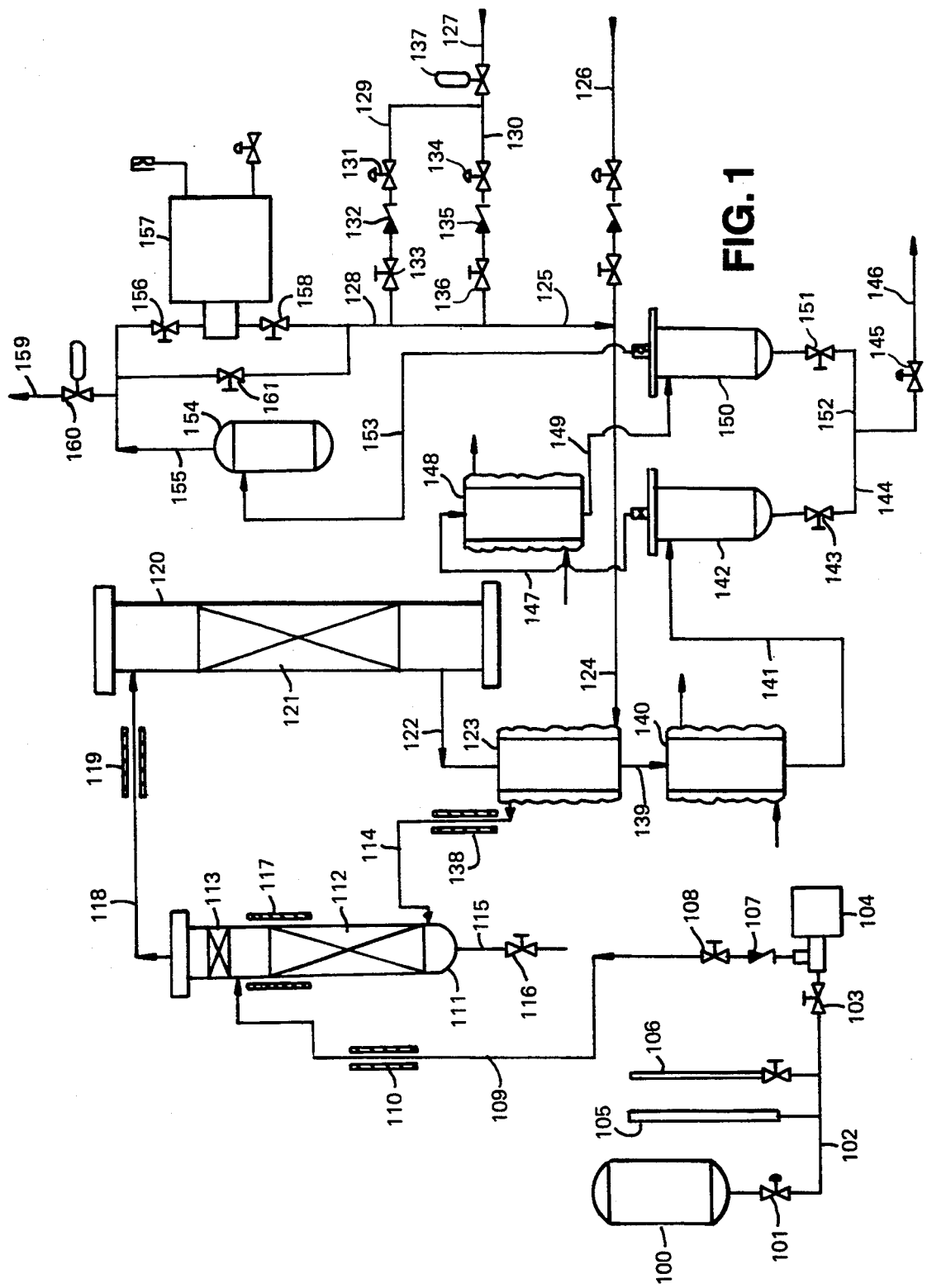
FIG. 1 is a simplified flow diagram of an experimental apparatus for production of 1,4-cyclohexanedimethanol in a single hydrogenation zone by hydrogenation of dimethyl 1,4-cyclohexanedicarboxylate.

The hydrogenation of a technical grade of dimethyl 1,4-cyclohexanedicarboxylate was investigated using the apparatus of FIG. 1. The composition of the technical grade feed was: 33.32 wt % trans-dimethyl 1,4-cyclohexanedicarboxylate, 61.89 wt % cis-dimethyl 1,4-cyclohexanedicarboxylate, 0.60 wt % methyl hydrogen 1,4-cyclohexanedicarboxylate of formula

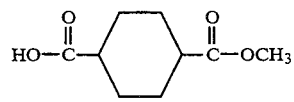

and 0.07 wt % water, with the balance being impurities.

In a commercial plant, hydrogen gas is advantageously recycled through the hydrogenation zone. The recycle hydrogen will contain a quantity of methanol vapour produced by the hydrogenation of dimethyl 1,4-cyclohexanedicarboxylate. Hence, the vaporous feed stream supplied to the hydrogenation zone in a commercial plant will generally contain methanol in addition to hydrogen and a hydrogenatable material. In order that the experimental rig described herebelow should accurately predict the likely results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described herebelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In all the Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 1. An approximately 70 wt % solution of the dimethyl 1,4-cyclohexanedicarboxylate feed is supplied from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm×6 mm glass rings 112. A stainless steel demister pad 113 is fitted at the top end of

TABLE I

| Catalyst | Composition wt % | | | | | | Surface area $m^2g$ | Density $g/cm^3$ | Pore volume $mm^3/g$ |
| --- | --- | --- | --- | --- | --- | --- | --- | --- | --- |
| | Cu | Cr | Zn | Mn | Ba | Al | | | |
| A DRD 89/21 | 57.6 | 19.0 | <0.01 | 0.09 | <0.01 | <0.01 | 28 | 1.420 | 200 |
| B DRD 92/89 | 41.1 | 0.26 | <0.01 | 6.4 | <0.01 | 20.4 | 47.1 | 1.452 | 211 | the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted manganese promoted copper on alumina hydrogenation catalyst 121. The catalyst was catalyst B of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) wrapped around reactor 120 under the control of appropriately positioned thermocouples (not shown) and by thermal insulation of the reactor 120. The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of catalyst was placed in reactor 120 which was then purged with nitrogen. The catalyst charge was then reduced carefully by a method similar to that described in EP-A-0301853.

The high purity dimethyl 1,4-cyclohexanedicarboxylate, appropriately spiked with the acidic material and diluted with methanol, was then pumped to the vaporiser 111 at a rate of 141 ml/h corresponding to a liquid hourly space velocity of 0.47 $h^{-1}$. The gas:dimethyl 1,4-cyclohexanedicarboxylate molar ratio in the vaporous mixture in line 118 was 477:1. The inlet temperature to reactor 120 was 223° C. and the inlet pressure was 901 psia (62.12 bar). The hydrogenation zone was therefore operated under conditions which prevented the condensation of both dimethyl 1,4-cyclohexanedicarboxylate and the less volatile 1,4-cyclohexanedimethanol product. The temperature throughout the hydrogenation zone was above the dew point at the operating pressure.

The liquid in line 146 was analysed by capillary gas chromatography using a 15 m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. The following compounds were detected in the reaction mixture: 1,4-cyclohexanedimethanol, dimethyl 1,4-cyclohexanedicarboxylate, 4-methoxymethyl cyclohexanemethanol, di-(4-methoxymethyl-cyclohexylmethyl) ether, and methanol. The acidity of the recovered reaction mixture was measured by titration. From the results obtained it was demonstrated that dimethyl 1,4-cyclohexanedicarboxylate had been converted in excess of 97.9%, while the acidic materials had been converted in excess of 99.5%, with a selectivity to 1,4-cyclohexanedimethanol of 99.35% being obtained, the balance being minor by-products. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction. The results are listed in Table II below, together with the results from Examples 2 and 3.

EXAMPLE 2

The feed was changed to a mixture of the technical grade of dimethyl 1,4-cyclohexanedicarboxylate and a quantity of a crude trans-dimethyl 1,4-cyclohexanedicarboxylate containing approximately 30 wt % of acidic materials comprising methyl hydrogen 1,4-cyclohexanedicarboxylate and 1,4-cyclohexanedicarboxylic acid. This mixture contained 6.50 wt % of acidic material as determined by titration. The results are noted in Table II.

EXAMPLE 3

The feed was switched back from the mixture used in Example 2 to the technical grade 1,4-cyclohexanedicarboxylate. The results are listed in Table II.

The run of each of Examples 1 to 3 lasted a number of hours during which no significant loss of catalyst activity was noted. Comparison of Examples 1 and 3 shows that essentially no loss of catalyst activity occurred during the three Examples; the slight change in conversion can be ascribed to the use of different liquid hourly space velocities in Examples 1 and 3 leading to a corresponding difference in residence time of the reaction mixture in contact with the hydrogenation catalyst.

TABLE II

| Example No. | MHCD wt % in feed-stock | Pressure psia (bar) | Inlet Temp. °C. | Gas:DMCD mol ratio | LHSV $h^{-1}$ | DMCD conversion mol % | CHDM trans-:cis- isomer ratio | Selectivity mol % CHDM | Selectivity mol % Byproducts |
|---|---|---|---|---|---|---|---|---|---|
| 1 | 1.6 | 901 (62.12) | 223 | 477 | 0.47 | 98.89 | 2.88 | 99.35 | 0.65 |
| 2 | 6.4 | 899 (61.98) | 225 | 498 | 0.50 | 98.49 | 2.92 | 99.36 | 0.64 |
| 3 | 1.6 | 901 (62.12) | 223 | 493 | 0.50 | 98.12 | 2.66 | 99.17 | 0.83 |

Notes to Table II:
MHCD = methyl hydrogen 1,4-cyclohexanedicarboxylate
DMCD = dimethyl 1,4-cyclohexanedicarboxylate
LHSV = liquid hourly space velocity
CHDM = cyclohexanedimethanol
Gas = hydrogen-containing gas containing more than 98% v/v hydrogen

EXAMPLES 4 to 7

Comparison Examples

Using a similar apparatus and procedure to that described in Example 1, four further runs were made using a charge of 250 ml of catalyst A of Table I. The results are tabulated below in Table III. The Notes to Table II apply also to Table III. Catalyst A is also available from Davy Research and Development Limited.

TABLE III

| Example No. | MHCD wt % in feed-stock | Pressure psia (bar) | Inlet Temp. °C. | $H_2$:DMCD mol ratio | LHSV $h^{-1}$ | DMCD conversion mol % | CHDM trans-:cis- isomer ratio | Selectivity mol % CHDM | Selectivity mol % Byproducts |
|---|---|---|---|---|---|---|---|---|---|
| 4 | 1.43 | 899 (61.98) | 220 | 527 | 0.31 | 98.06 | 2.62 | 99.20 | 0.80 |
| 5 | 3.14 | 903 (62.26) | 220 | 524 | 0.31 | 96.76 | 2.44 | 99.03 | 0.97 |
| 6 | 6.28 | 903 (62.26) | 220 | 549 | 0.31 | 90.64 | 2.02 | 99.27 | 0.73 |
| 7 | 1.43 | 900 (62.05) | 220 | 543 | 0.30 | 97.23 | 2.44 | 99.18 | 0.82 |

Figure 2:
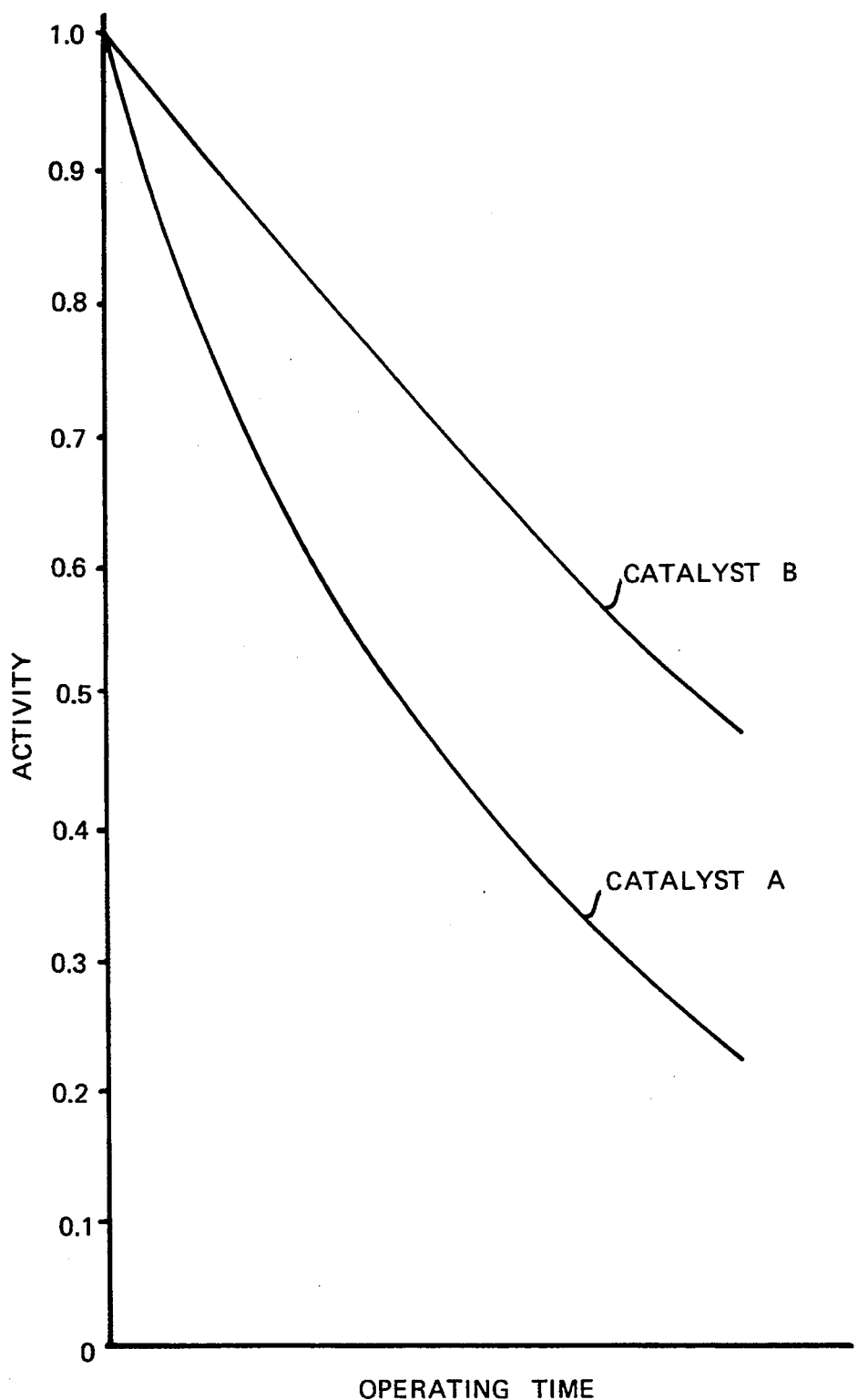
FIG. 2 is a plot of catalyst activity against time for a reduced manganese promoted copper catalyst and for a reduced copper chromite catalyst using an acidic dimethyl 1,4-cyclohexanedicarboxylate feedstock.

In FIG. 2 there are plotted the results obtained using a feed of dimethyl 1,4-cyclohexanedicarboxylate containing about 1.59 wt % of methyl hydrogen 1,4-cyclohexanedicarboxylate during respective extended runs using catalysts A and B. Each catalyst was assigned an initial activity of 1.0 based on the conversion of dimethyl 1,4-cyclohexanedicarboxylate at a standard set of conditions. It was ascertained that catalyst was about 30% to about 40% more productive than catalyst A for the production of 1,4-cyclohexanedimethanol from dimethyl 1,4-cyclohexanedicarboxylate by hydrogenation. FIG. 2, which is a plot of the fraction of activity remaining against time of operation plotted on the same scale for both catalysts, shows clearly that the rate of loss of activity is significantly greater for catalyst A than for Catalyst B.

We claim:

1. A process for the production of cyclohexanedimethanol by hydrogenation of dialkyl cyclohexanedicarboxylate which comprises the steps of:
   (a) providing a hydrogenation zone containing a charge of a granular reduced manganese promoted copper catalyst;
   (b) forming a vaporous feed stream of a hydrogenatable material comprising a dialkyl cyclohexanedicarboxylate and from about 0.1 wt % up to about 15 wt % of an acidic material at a feed temperature which is in the range of from about 150° C. to about 350° C. and which is above the dew point of the feed stream and at a feed pressure which is in the range of from about 150 psia (about 10.34 bar) up to about 2000 psia (about 137.90 bar), said vaporous mixture having a known hydrogen-containing gas:dialkyl cyclohexanedicarboxylate ratio;
   (c) supplying the vaporous feed stream to the hydrogenation zone;
   (d) maintaining hydrogenation conditions in the hydrogenation zone which are effective to maintain the reaction mixture in contact with the catalyst above its dew point;
   (e) passing the vaporous feed stream through the hydrogenation zone: and
   (f) recovering from the hydrogenation zone a product stream comprising cyclohexanedimethanol;
   wherein the dialkyl cyclohexanedicarboxylate is selected from di-($C_1$ to $C_4$ alkyl) cyclohexanedicarboxylates.

2. A process according to claim 1, in which the dialkyl cyclohexanedicarboxylate is dimethyl cyclohexanedicarboxylate and in which the acidic material comprises methyl hydrogen cyclohexanedicarboxylate and/or cyclohexanedicarboxylic acid.

3. A process according to claim 2, in which the hydrogen-containing gas:dialkyl cyclohexanedicarboxylate molar ratio in the vaporous feed mixture is in the range of from about 200:1 to about 1000:1.

4. A process according to claim 3, in which the feed temperature is in the range of from about 150° C. to about 300° C.

5. A process according to claim 4, in which the feed temperature is in the range of from about 200° C. to about 260° C.

6. A process according to claim 5, in which the feed pressure is in the range of from about 450 psia (about 31.03 bar) to about 1000 psia (about 68.95 bar).

7. A process according to claim 6, in which the dialkyl cyclohexanedicarboxylate is supplied to the hydrogenation zone at a rate corresponding to a liquid hourly space velocity of from about 0.05 to about 4.0 h$^{-1}$.

8. A process according to claim 7, in which the hydrogenatable material comprises from about 1 wt % up to about 10 wt % alkyl hydrogen cyclohexanedicarboxylate and/or cyclohexanedicarboxylic acid.

9. A process according to claim 8, in which the hydrogenatable material comprises from about 2.5 wt % up to about 5 wt % alkyl hydrogen cyclohexanedicarboxylate and/or cyclohexanedicarboxylic acid.

10. A process for the production of cyclohexanedimethanol by hydrogenation of dimethyl cyclohexanedicarboxylate which comprises the steps of:
   (a) providing a hydrogenation zone containing a charge of a granular reduced manganese promoted copper catalyst;
   (b) forming a vaporous feed stream of a hydrogenatable material comprising dimethyl cyclohexanedicarboxylate and from about 0.1 wt % up to about 15 wt % of an acidic material selected from methyl hydrogen cyclohexanedicarboxylate and/or cyclohexanedicarboxylic acid at a feed temperature which is in the range of from about 150° C. to about 350° C. and which is above the dew point of the feed stream and at a feed pressure which is in the range of from about 150 psia (about 10.34 bar) up to about 2000 psia (about 137.90 bar), said vaporous mixture having a known hydrogen-containing gas:dialkyl cyclohexanedicarboxylate ratio;
   (c) supplying the vaporous feed stream to the hydrogenation zone;
   (d) maintaining hydrogenation conditions in the hydrogenation zone which are effective to maintain the reaction mixture in contact with the catalyst above its dew point;
   (e) passing the vaporous feed stream through the hydrogenation zone; and
   (f) recovering from the hydrogenation zone a product stream comprising cyclohexanedimethanol.

11. A process according to claim 10 for the production of cyclohexanedimethanol by hydrogenation of dimethyl cyclohexanedicarboxylate the feed temperature is in the range of about 150° C. to about 300° C. and the feed pressure is in the range of about 450 psia (about 31.03 bar) up to about 1000 psia (about 68.95 bar) and the manganese promoted copper catalyst has a Cu:Mn weight ratio of from about 2:1 to about 10:1.

12. A process according to claim 11 for the production of cyclohexanedimethanol by hydrogenation of dimethyl cyclohexanedicarboxylate the feed temperature is in the range of about 200° C. to about 260° C.

13. A process according to claim 11, in which the dimethyl cyclohexanedicarboxylate comprises cis-dimethyl 1,4-cyclohexanedicarboxylate and the hydrogenatable material comprises methyl hydrogen 1,4-cyclohexanedicarboxylate and/or 1,4-cyclohexanedicarboxylic acid.

14. A process according to claim 11, in which the dimethyl cyclohexanedicarboxylate comprises trans-dimethyl 1,4-cyclohexanedicarboxylate and the hydrogenatable material comprises methyl hydrogen 1,4-cyclohexanedicarboxylate and/or 1,4-cyclohexanedicarboxylic acid.

15. A process according to claim 11, in which the dimethyl cyclohexanedicarboxylate comprises a mixture of the cis- and trans- isomers of dimethyl 1,4-cyclohexanedicarboxylate and the hydrogenatable material comprises methyl hydrogen 1,4-cyclohexanedicarboxylate and/or 1,4-cyclohexanedicarboxylic acid.

16. A process according to claim 11, in which the vaporous mixture comprises dimethyl 1,3-cyclohexanedicarboxylate and the hydrogenatable material comprises methyl hydrogen 1,3-cyclohexanedicarboxylate and/or 1,3-cyclohexanedicarboxylic acid.

17. A process according to claim 11, in which the vaporous mixture comprises dimethyl 1,2-cyclohexanedicarboxylate and the hydrogenatable material comprises methyl hydrogen 1,2-cyclohexanedicarboxylate and/or 1,2-cyclohexanedicarboxylic acid.

* * * * *